US005837808A

United States Patent [19]

Ku et al.

[11] Patent Number: 5,837,808

[45] Date of Patent: Nov. 17, 1998

[54] ANALOGS OF HIRUDIN

[75] Inventors: Cecilia S. L. Ku, Lake Forest; Richard Johnson; Julian P. Breillatt, Jr., both of Mundelein, all of Ill.

[73] Assignee: Baxter International Inc., Deerfield, Ill.

[21] Appl. No.: 492,343

[22] Filed: Jun. 19, 1995

Related U.S. Application Data

[63] Continuation of Ser. No. 116,939, Sep. 7, 1993, abandoned, which is a continuation-in-part of Ser. No. 747,565, Aug. 20, 1991, abandoned.

[51] Int. Cl.[6] .................... C07K 14/00

[52] U.S. Cl. .................... 530/324; 530/811; 530/812; 530/813; 530/816; 514/12; 514/2

[58] Field of Search .................... 530/324, 350, 530/325, 811, 812, 813, 816; 525/54.1; 523/112; 514/12, 2; 930/260, 280

[56] References Cited

U.S. PATENT DOCUMENTS

| | | | |
|---|---|---|---|
| 4,745,177 | 5/1988 | Fritz et al. | 514/12 |
| 4,767,742 | 8/1988 | Dodt et al. | 514/12 |
| 4,791,100 | 12/1988 | Kramer et al. | 514/12 |
| 4,801,576 | 1/1989 | Fritz et al. | 514/12 |
| 5,112,615 | 5/1992 | Ito et al. | 424/426 |

FOREIGN PATENT DOCUMENTS

| | | |
|---|---|---|
| 86102462 | 2/1986 | European Pat. Off. . |
| 86400961 | 11/1986 | European Pat. Off. . |
| 87401649 | 7/1987 | European Pat. Off. . |
| 87402696 | 11/1987 | European Pat. Off. . |
| 893021592 | 3/1989 | European Pat. Off. . |
| 894006212 | 3/1989 | European Pat. Off. . |
| 89105218 | 7/1989 | European Pat. Off. . |
| 898105226 | 7/1989 | European Pat. Off. . |
| 893079228 | 8/1989 | European Pat. Off. . |
| 898106760 | 9/1989 | European Pat. Off. . |
| 893110221 | 10/1989 | European Pat. Off. . |
| 891224511 | 12/1989 | European Pat. Off. . |
| WO8504418 | 10/1985 | WIPO . |

OTHER PUBLICATIONS

DiMaio, J. et al., "Bifunctional Thrombin Inhibitors Based on the Sequence of Hirudin," J. Biol. Chem., vol. 265, No. 35, pp. 21698–21703 (1990).

Johnson, P. H. et al., "Biochemistry and Genetic Engineering of Hirudin," Seminars in Thrombosis and Hemostasis, vol. 15, No. 3, 1989.

Lazar, J. B. et al., "Hirudin:Amino–Terminal Residues Play a Major Role in the Interaction with Thrombin," J. Biol. Chem., vol. 266, No. 2 pp. 685–688 (1991).

Maraganore, J. M. et al., "Design and Characterization of Hirulogs:A Novel Class of Bivalent Peptide," Abstract presented symposium Biomedical Horizons of the Leech, Oct. 24–28, 1990.

Maraganore, J. M., et al., "Design and Characterization of Hirulogs:A Novel Class of Bivalent Peptide Inhibitors of Thrombin," Biochemistry 29, pp. 7095–7101 (1990).

Markwardt, F. "Development of Hirudin as an Antithrombotic Agent," Seminars in Thrombosis and Hemostatis, vol. 15, No. 3, pp. 269–282 (1989).

Rydel, T. J. et al., "The Structure of a Complex of Recombinant Hirudin and Human Antithrombin," Science, 249, pp. 277–280 (1990).

Krstenansky, J.L. et al., J. Med. Chem. 30, pp. 1688 to 1691 (1987).

*Primary Examiner*—Ponnathapura Achutamurthy
*Assistant Examiner*—T. D. Wessendorf
*Attorney, Agent, or Firm*—Mark J. Buonauito; Joseph A. Fuchs

[57] ABSTRACT

A tyrosine-substituted hirudin analog has antithrombogenic activity. Further simultaneous reaction at native tyrosine residues is prevented by mutation at those sites to encode nonreactive amino acids. Several novel strategies for coupling the hirudin analog to solid surfaces while simultaneously conserving antithrombogenic activity are disclosed.

1 Claim, 2 Drawing Sheets

Coding sequence of rHV2-Phe[3] Gln[33] Tyr[35] Lys[47] Asp[63]

```
                                                 ATTACGTTCACAGAC
                                                 ----+----.----+   2000
                                                 TAATGCAAGTGTCTG

                                                 IleThrPheThrAsp
                                                 1     3

TGCACAGAATCGGGTCAAAATTTGTGCCTCTGCGAGGGAAGCAATGTTTG
----.----+----.----+----.----+----.----+----.----+   2050
ACGTGTCTTAGCCCAGTTTTAAACACGGAGACGCTCCCTTCGTTACAAAC

CysThrGluSerGlyGlnAsnLeuCysLeuCysGluGlySerAsnValCys
            10                            20

CGGTAAAGGCAATAAGTGCATATTGGGTTCTCAAGGATACGGCAACCAAT
----.----+----.----+----.----+----.----+----.----+   2100
GCCATTTCCGTTATTCACGTATAACCCAAGAGTTCCTATGCCGTTGGTTA

 GlyLysGlyAsnLysCysIleLeuGlySerGlnGlyTyrGlyAsnGlnCys

                      30        33    35

GTGTCACTGGCGAAGGTACACCGAAACCTGAAAGCCATAATAACGGCGAT
----.----+----.----+----.----+----.----+----.----+   2150
CACAGTGACCGCTTCCATGTGGCTTTGGACTTTCGGTATTATTGCCGCTA

  ValThrGlyGluGlyThrProLysProGluSerHisAsnAsnGlyAsp
  40                             50

TTCGAAGAAATTCCAGAAGAAGACTTACAATGAaaaatg
----.----+----.----+----.----+----.----   2189
AAGCTTCTTTAAGGTCTTCTTCTGAATGTTACTttttac

PheGluGluIleProGluGluAspLeuGln***
            60       63
```

FIG. 1

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 204 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..195

( x i ) SEQUENCE DESCRIPTION: SEQ ID NO:1:

```
ATT ACG TTC ACA GAC TGC ACA GAA TCG GGT CAA AAT TTG TGC CTC TGC      48
Ile Thr Phe Thr Asp Cys Thr Glu Ser Gly Gln Asn Leu Cys Leu Cys
 1               5                  10                  15

GAG GGA AGC AAT GTT TGC GGT AAA GGC AAT AAG TGC ATA TTG GGT TCT      96
Glu Gly Ser Asn Val Cys Gly Lys Gly Asn Lys Cys Ile Leu Gly Ser
            20                  25                  30

CAA GGA TAC GGC AAC CAA TGT GTC ACT GGC GAA GGT ACA CCG AAA CCT     144
Gln Gly Tyr Gly Asn Gln Cys Val Thr Gly Glu Gly Thr Pro Lys Pro
        35                  40                  45

GAA AGC CAT AAT AAC GGC GAT TTC GAA GAA ATT CCA GAA GAA GAC TTA     192
Glu Ser His Asn Asn Gly Asp Phe Glu Glu Ile Pro Glu Glu Asp Leu
    50                  55                  60

CAA TGAAAAATG                                                       204
Gln
 65
```

( 2 ) INFORMATION FOR SEQ ID NO:2:

( i ) SEQUENCE CHARACTERISTICS:
( A ) LENGTH: 65 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Ile Thr Phe Thr Asp Cys Thr Glu Ser Gly Gln Asn Leu Cys Leu Cys
 1               5                  10                  15

Glu Gly Ser Asn Val Cys Gly Lys Gly Asn Lys Cys Ile Leu Gly Ser
            20                  25                  30

Gln Gly Tyr Gly Asn Gln Cys Val Thr Gly Glu Gly Thr Pro Lys Pro
        35                  40                  45

Glu Ser His Asn Asn Gly Asp Phe Glu Glu Ile Pro Glu Glu Asp Leu
    50                  55                  60

Gln
 65
```

ANALOGS OF HIRUDIN

This is a continuation of application Ser. No. 08/116,939, filed on Sep. 7, 1993, now abandoned which, is a continuation-in-part of U.S. application Ser. No. 07/747,565, filed Aug. 20, 1991, now abandoned.

TECHNICAL FIELD

This invention relates to analogs of hirudin and in particular relates to, analogs of hirudin which have antithrombogenic activity and which can be bound to polymers.

BACKGROUND ART

Natural hirudin is a mixture of closely related polypeptides each containing approximately 64 to 66 amino acids and having a molecular weight of approximately 6900 daltons. At least 20 natural variants of hirudin have been identified. Scharf et al., FEBS Letters 255 pp. 105 to 110 (September 1989). It is produced by the European medicinal leech *Hirudo medicinalis*. It prevents blood from clotting by forming an inhibitory 1:1 molecular complex with activated thrombin (approximately $K_{iApp=}10^{-11}$to $10^{-14}$M). Hirudin forms a very tight complex with thrombin, wherein over 40% of the hirudin structure intimately contacts the thrombin molecule and covers both the fibrinogen recognition site of thrombin and the fibrinogen cleaving (active) site of thrombin. Twenty-seven of the sixty-five residues of hirudin have contacts less than 4.0 Å with thrombin. This close fit prevents both the binding and cleavage of fibrinogen by thrombin.

It is impractical to prepare natural hirudin in quantities necessary for therapeutic use. At least three recombinant hirudins are now available identical to native variants, except the recombinants lack the sulphate residue on the tyrosine at position 63 found in native variants. These recombinant hirudins show pharmacological properties very similar to native hirudin (Markwardt, Sem. Thromb. Hemostas. 15, pp. 269 to 282 (1989)). European Patent Application 87402696.6 shows the amino acid sequence of hirudin variants 1, 2, and 3 (HV1, HV2 & HV3).

Three regions of the hirudin molecule are now believed to be essential to the thrombin-hirudin high affinity interaction based on X-ray crystallography (Rydel, et al., Science 249 (1990) pp. 277 to 280) and structure-activity studies (Krstenansky, et al., J. Med. Chem. 30 (1987) pp. 1688 to 1691). First, the three $NH_2$-terminal amino acid residues at positions 1, 2, and 3 of hirudin form a parallel beta strand with $Ser^{214}$ to $Glu^{217}$ of thrombin and participate in several dozen non-polar interactions with side chains of amino acids in and around the active site of thrombin. Second, the $NH_2$-terminal domain of hirudin from approximately $Thr^{4}$ to $Pro^{148}$ is a compactly folded structure composed of four loops stabilized by three disulfide bridges and antiparallel beta structures. The main function of this domain is to position and facilitate the interaction of hirudin's $NH_2$-terminal tripeptide at the thrombin active site. Third, the COOH-terminal tail of hirudin ($Glu^{49}$-$Pro^{60}$) binds in the anion-binding exosite of thrombin and terminates in a hydrophobic helical turn defined by the sequence $Glu^{61}$-$Leu^{64}$. The exosite constitutes the fibrinogen binding recognition site of thrombin and is dominated by numerous polar and non-polar interactions. The presence of hirudin in the exosite prevents fibrinogen from being recognized.

Most research on the hirudin molecule has focussed on (i) determining the roles of various regions of the molecule in its interaction with thrombin, and (ii) making modifications to the molecule to increase the binding affinity between hirudin and thrombin and thereby reduce the necessary dose in therapeutic applications. Some research has focussed on prolonging the activity or half-life of hirudin in vivo, and other research has been in the area of immobilizing hirudin on surfaces used in medical devices which come in contact with blood to provide a non-thrombogenic surface.

a. Modifications to Increase Binding Affinity or to Prolong In Vivo Half-Life of Hirudin PCT Application WO 85/04418 discloses recombinant HV2 where $Lys^{24}$, $Asn^{33}$, $Lys^{35}$, $Gly^{36}$, $Asn^{47}$, $Glu^{49}$, and $Asn^{53}$ are replaced by Gln, Asp, Glu, Lys, Lys, Gln, and Asp respectively.

European Patent Application No. 87402696.6 discloses recombinant variants 1, 2, and 3 where Tyr 63 or 64 is replaced by Glu or Asp and Lys 47 or Asn 47 is replaced by Arg or His.

European Patent Application No. 89400621.2 also discloses amino acid sequence modifications, including those at positions 1, 2, 33, 35, 36, 47, and 63, which increase the in vivo half life of the molecule, increase the specificity of the molecule's interaction with cell surface receptors and increase resistance to carboxypeptidase degradation. Arg is placed in the 33 position, Thr or Ser or Asp are placed at position 35, and Ser is placed at position 36.

European Patent Application No. 89810521.8 describes mutations at the 53, 57, 58, 61, 62, and 63 positions which, depending upon the analog selected, provide increased or decreased antithrombogenic activity.

U.S. Pat. No. 4,179,337 discloses the attachment of mass-increasing molecules such as polyethylene glycol to proteins.

Lazar, et al. describe mutations at position 3 in recombinant hirudin variant 1 (rHV1) where antithrombin activity was increased by replacing Tyr with Phe or Trp, and markedly decreased by replacement with Thr (J. B. Lazar, R. C. Winant & P. H. Johnson. J. Biol. Chem. 266 pp. 685–688 (1991)).

Johnson, P. H. et al. in "Biochemistry and Genetic Engineering of Hirudin", Seminars in Thrombosis and Hemostasis, Vol. 15 No. 13 (1989) at pp. 309 describes hirudin fragments having antithrombogenic activity. These fragments correspond to residues 42 to 65 and 51 to 65.

European Patent Application No. 89810522.6 describes mutations at positions 1, 27, 36, 47, 48, 49, 51 and 52. The substitution at 36 is Lys, Arg, Asn, Val, Leu or Gln. The substitution at 27 is Gln, Asn, Leu, Arg, or Val. The substitution at 49 is Asn or Met. The substitution at 47 is Arg, Asn, Val, or Leu.

European Patent Application No. 89810676.0 describes mutations at positions 1, 2, 27, 36, 47, 57, 58, 61, and 66 where the position 27 substitution is Gln, position 36 substitution is Gln and position 47 substitution is Arg.

The following references disclose modifications at the C-terminal and N-terminal ends of the hirudin molecule: European Patent No. 142860; U.S. Pat. No. 4,801,576; U.S. Pat. No. 4,745,177; U.S. Pat. No. 4,767,742, and European Application No. 86102462.8.

U.S. Pat. No. 4,791,100 discloses mutations of hirudin in positions corresponding to, inter alia, 35 and 36, where at 35 the substitution is Glu and at 36 the substitution is Lys. It also discloses analogs having a greater number of amino acids than native hirudin and others having fewer amino acids than native hirudin.

b. Immobilization of Hirudin on Surfaces

European Application No. 89311022.1, European Application No. 89307922.8 to Ito, and references cited therein disclose the attachment of hirudin to surfaces. The data disclosed in the Ito application shows substantial loss of antithrombogenic activity occurred when the molecule was immobilized on the surface.

c. Fragments

Various COOH-terminal polypeptide fragments of hirudin are known to bind to thrombin, thereby inhibiting the binding and cleavage of fibrinogen by thrombin. The minimum length polypeptide required to exert inhibitory activity has been reported as Phe $^{56}$-Gln$^{65}$ (J. L. Krstenansky, T. J. Owen, M. T. Yates & S. J. T. Mao. J. Med Chem 30 pp. 1688–1691 (1987)). Addition of amino acid residues to this polypeptide to increase its length and provide the amino acid sequences found in the several hirudin variants up to and including the complete sequences Glu$^{49}$-Gln$^{65}$ augments the thrombin inhibitory activity of the fragments; and, the sequence may be extended to include Gly$^{42}$-Gln$^{65}$ without compromising the efficacy of the inhibitor. Moreover, the deletion of Gln from the polypeptides of these series provides an analogous series of useful thrombin inhibitory peptides.

In a further extension of this reasoning, numerous synthetic variations of the polypeptide sequences found in the natural hirudin variants (peptidomimetic analogs of hirudin peptides) have been prepared and found to possess thrombin inhibitory activity. Notable among them are those described in European Patent Application No. 89302159.2 and others utilizing non-protein amino acids (European Patent Application No. 89122451.1).

Maraganore, J. M. et al. in an abstract presented at a symposium entitled "Biomedical Horizons of the Leech" on Oct. 24–28, 1990 disclose synthetic peptides which bind to both the anion binding exosite and the active site. The peptides are called "hirulogs" and consist of (i) an active-site specificity sequence, (ii) a poly-Gly linker, and (iii) an anion binding exosite recognition sequence.

There are many variations possible on this model of bivalent thrombin inhibitors and in general, bivalent protease inhibitors. For example see J. M. Maraganore, P. Bourdon, J. Jablonski, K. L. Ramachandran and J. W. Fenton, II. Biochemistry 29 pp. 7095–7101 (1990); J. DiMaio, B. Gibbs, D. Munn, J. Lefebvre, F. Ni, and Y. Konishi. J. Biol. Chem. 265 pp. 21698–21703 (1990).

European Application No. 89302160.0 discloses peptides of about 8 to 26 amino acids having the biological activity of hirudin.

European Application No. 89302159.2 discloses cyclicized synthetic fragments of hirudin having antithrombogenic activity.

It is a primary object of this invention to provide antithrombogenic hirudin analogs having amino acids available for attachment of spacer molecules. The analogs can be bound to a surface via a spacer molecule rendering the surface nonthrombogenic. Alternatively, the analogs can be bound to a polymer via a spacer molecule to increase the analogs' in vivo half life. It is a further object of this invention to provide nonthrombogenic materials comprising such analogs attached to surfaces. It is a further object of this invention to provide analogs attached to polymers.

BRIEF DESCRIPTION OF THE FIGURES

FIG. 1 shows the amino acid sequence of HV2-Phe$^3$ Gln$^{33}$ Tyr$^{35}$ Lys$^{47}$ Asp$^{63}$ and its encoding DNA sequence (SEQ ID NOS: 1&2).

SUMMARY OF THE INVENTION

Figure 2:
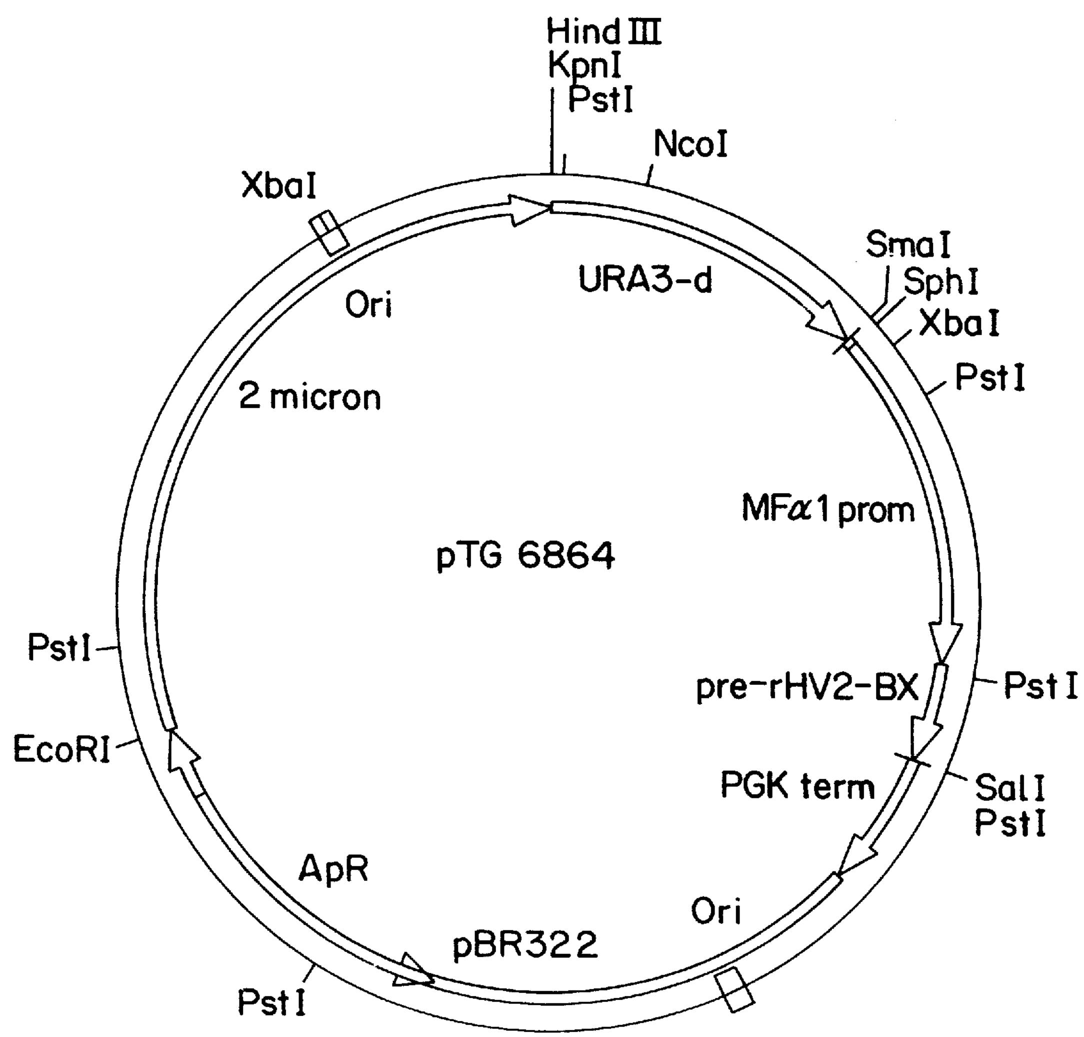
FIG. 2 depicts the expression vector for the sequence in FIG. 1.

The present invention provides an analog of hirudin having at least one amino acid in positions 30 to 37 substituted with Tyr, and the native Tyr$^3$ and Tyr$^{63 or 64}$ residues substituted with a first and a second functional nonreactive amino acid.

A preferred embodiment of the invention is an analog of hirudin having at least one amino acid in positions 32 to 36 substituted with Tyr, the native Tyr$^3$ substituted with Phe, Ile or Leu, and Tyr$^{63 or 64}$ substituted with Asp or Glu.

As used herein the term analog includes fragments and analogs of hirudin wherein a tyrosine residue is attached to the $NH_2$-terminal position of such analogs, and the residue equivalent to Tyr$^{63}$, when present, is substituted with either Glu or Asp.

As used herein the term analog includes peptidomimetic analogs of hirudin which are bivalent inhibitors of thrombin, where a tyrosine residue is inserted in or near the oligomer that links the COOH-terminal hirudin peptide mimic to the peptide that binds in the active site of thrombin, and where a functional nonreactive amino acid, preferably Asp or Glu, replaces the residue equivalent to Tyr$^{63}$.

The present invention also overcomes the disadvantages of the prior art by providing an antithrombogenic hirudin analog covalently attached to a spacer molecule at a reactive nonfunctional Tyr residue of the analog.

The present invention further provides Applicant's novel analogs attached to surfaces rendering such surfaces nonthrombogenic.

The present invention further provides Applicant's novel analogs attached to mass-increasing molecules, which will have a prolonged half-life in vivo.

DETAILED DESCRIPTION OF THE INVENTION

The present invention provides analogs of hirudin having at least one "reactive" amino acid in positions 30 to 37 and having a "functional" but "nonreactive" amino acid at positions 3 and 63. A prominent loop or finger region extends out away from the hirudin-thrombin interface and contains at its tip the sequence Leu$^{30}$ Gly$^{31}$ Ser$^{32}$ Asn$^{33}$ Gly$^{34}$ Lys$^{35}$ Gly$^{36}$ Asn$^{37}$ (for hirudin variant 2). Amino acid substitutions in this region are believed not to affect the interaction of hirudin with thrombin. See European Patent Application No. 89400621.2 and Rydel, et al., Science 249 pp. 277 to 280 (1991). In accordance with the present invention this loop is a preferred site for substitution with Tyr to allow the attachment of a spacer molecule for surface immobilization of a hirudin analog to render the surface nonthrombogenic. Alternately, in accordance with the present invention, the novel hirudin analog may be bound to an oligomer, a polymer, a macromolecule, or other mass-increasing molecule, thereby increasing the effective molecular weight of hirudin and prolonging its in vivo half-life and its anticoagulative effect in the circulation when administered therapeutically.

To avoid reaction of the spacer molecules or mass-increasing molecule with Tyr in positions outside the finger region, where attachment to a molecule might destroy antithrombogenic activity, Tyr residues outside the finger region are substituted with amino acids that will not react with the spacer. As used herein, the term "nonreactive" shall mean an amino acid which, due to its nature and/or position within the analog, will not form a covalent bond with certain mass-increasing and spacer molecules described below. As used herein the term "functional" shall mean an amino acid in a particular position necessary for the analog to have antithrombogenic activity.

Hirudin includes a Tyr at positions 3 and 63 or 64, which are functional in the sense that they are believed to be necessary for the molecule to have antithrombogenic activity (See European Patent Application No. 87402696.6 and Lazar et al., op. cit.). However, the native Tyr at 3 and 63 are also reactive. If not substituted these amino acids will react with the spacer or mass-increasing molecule rendering the product ineffective as an antithrombogenic agent. European Patent Application Nos. 87402696.6 and 89810521.8 suggest that the substitution of Asp or Glu for the native Tyr at position 63 will not destroy the antithrombogenic activity of the analog. X-ray crystallographic studies showed that in a hirudin-thrombin complex, $Tyr^3$ of hirudin occupies a hydrophobic cleft adjacent to the active site of thrombin that is occupied in a similar manner by the Phe residue of the thrombin inhibitor, PPACK (Phe-Pro-Arg-chloromethylketone) (Rydel, et al., op. cit.) This suggests that substitution of Phe for $Tyr^3$ would not significantly reduce the antithrombogenic activity of the analog.

Accordingly, in the analog of the present invention, the functional $Tyr^3$ and $Tyr^{63}$ are replaced with functional yet nonreactive amino acids to prevent reaction of the spacer or mass-increasing molecule at the functional positions. The preferred functional, nonreactive amino acids for position 3 in hirudin are Phe, Leu and Ile. The preferred functional, nonreactive amino acids for position 63 or 64 are Asp and Glu. When both the finger region substitution and these terminal substitutions are made the result is an analog having Tyr available for reaction with a spacer or mass-increasing molecule in the nonfunctional finger region and functional, yet nonreactive amino acids in positions 3 and 63 or 64.

In a preferred embodiment Tyr is placed at position 35 in hirudin. Tyr may also preferably be placed at position 33.

As disclosed in European Application No. 87402696.6, in hirudin variant 2 native Asn at 47 may be substituted with Lys to enhance the binding affinity of the molecule to thrombin.

The present invention requires at least one nonfunctional amino acid available for reaction. The inclusion of additional nonfunctional reactive Tyr substitutions may enhance the usefulness of the analog for chemical attachment to surfaces or in promoting increased in vivo half life of the analog. Those skilled in the art using routine experimentation will be able to determine whether the introduction of too many of the disclosed Tyr substitutions in the analog will impair its usefulness in chemical attachment to surfaces or to mass-increasing macromolecules, due to, for example, steric hindrance of the portions of the analog which bind to thrombin.

The analogs of the present invention may be prepared using recombinant DNA techniques known to those skilled in the art, for example, by subjecting the gene that codes for hirudin to site-specific mutagenesis and expressing the mutated gene in a suitable host such as a yeast or bacterium. European Patent No. 200655 discloses an expression system for hirudin in yeast. The plasmid used to transform the yeast may be altered by methods known to those skilled in the art to create the novel mutations described herein. European Patent Application Nos. 89810521.8 and 89810522.6 of Ciba Geigy AG and patent applications cited therein disclose microbial hosts for vectors containing hirudin DNA sequences. The analog described in Example 1 below was made by the methods disclosed in European Patent Applications Nos. 87401649.6 and 89400621.2.

Those skilled in the art will understand that fragments of the hirudin molecule, COOH-terminal polypeptide fragments, peptidomimetic analogs, and bivalent inhibitors (as described above in the section entitled "Fragments") may also be modified according to the criteria of the present invention provided that such "fragment" has at least one site where a Tyr may be substituted without eliminating the antithrombin activity of the "fragment", and further provided that the functional groups on the "fragment" are either nonreactive or can be substituted with a functional nonreactive amino acid. Fragments or peptides having such activity and modifications thereof fall within the intent and scope of the present invention. Accordingly, the term analog as used herein shall include a fragment of the hirudin molecule, peptidomimetic analogs, and bivalent inhibitors having antithrombogenic activity. The term analog as used herein shall include a synthetic peptide having antithrombogenic activity by virtue of an amino acid sequence analogous to that of the functional portions of the native hirudin molecule.

For example, the $NH_2$-terminal end of the hirudin peptides and peptidomimetic analogs known to inhibit thrombin activity has a lesser influence on their effectiveness than the COOH-terminal residues. See Johnson, P. H. et al. in "Biochemistry and Genetic Engineering of Hirudin", Seminars in Thrombosis and Hemostasis, Volume 15, No 13 (1989) and J. L. Krstenansky, T. J. Owen, M. T. Yates, and S. J. T. Mao, J. Med. Chem. 30, PP. 1688–1691 (1987). Attachment of a Tyr residue to the $NH_2$-terminal end or equivalent region of these various inhibitory polypeptides, and peptidomimetic analogs, accompanied by substitution of the Tyr equivalent residue by Asp or Glu, provides a unique attachment site for an immobilizing spacer molecule or mass-increasing molecule according to the methods of this invention.

The bivalent thrombin inhibitors described by Maraganore et al., Biochem. 29, pp. 7095 to 7101 (1990) offer design flexibility in the placement of a reactive amino acid residue for attachment of spacer or mass increasing molecules. A tyrosine residue inserted in or near the oligoglycine connecting link that joins the active site binding moiety with the longer peptide that binds in the fibrinogen recognition site provides a unique site for attaching a spacer, when in accordance with this invention, the $Tyr^{63}$ equivalent residue is replaced with Glu or Asp.

Tyr is used for spacer attachment because it provides for site specific chemical reactions that avoid binding the spacer to other residues that could interfere with hirudin's activity. The specificity of these reactions depends on the altered reactivity of groups inserted into the phenolic ring of Tyr. A preferred means to attach a spacer to a Tyr residue is to insert a primary amine into its phenolic ring. Many reagents developed for derivatization and immobilization of proteins are designed to react with primary amino groups in their neutral, unprotonated state. Use of these reagents with hirudin under usual derivatization conditions will impair the antithrombin activity of hirudin by attaching spacer molecules to its $NH_2$-terminal amine or to certain of its lysyl epsilon-amino groups. An aryl amine on Tyr avoids these drawbacks by reacting with amine reactive agents under conditions that virtually exclude reactivity with the alkyl amines of Lys and the $NH_2$-terminal amino acid residue. An aryl amine of Tyr has a $pK_a$ of about 4.8, i.e., it is 50% protonated at pH 4.8. Since the protonated form of a primary amine is unreactive to the commonly used spacer attachment chemistries, the tyrosyl amine residue will react at about 50% efficiency at pH 5.0. However, at pH 5.0, less than 0.1% of the alpha-amine of the $NH_2$-terminal residue ($pK_a$ about 8.0), and less than 0.001% of the epsilon-amine of Lys ($pK_a$ about 10.0) will be reactive with such spacer chemistries. This provides the site-specificity. However, chemical methods that insert an amine into the phenolic ring of Tyr may also react with Trp and free Cys; however, hirudin has no Trp residues and all 6 Cys residues are engaged in unreactive disulfide bridges. Therefore, specific reactivity with Tyr is obtained.

A less preferred means to attach spacers to Tyr uses spacers activated with diazonium salts, which react directly and efficiently with the phenolic ring of Tyr. However, this reaction is not specific to Tyr, since His residues also react and hirudin's only His is essential to thrombin binding. Other less preferred spacer chemistries used to attach spacers to Tyr residues are photo-oxidation, N-bromosuccinimide and sulfonyl halides which also react with amino acid side chains other than Tyr.

Spacers capable of reacting predominantly with aryl amines rather than with alkyl amines at about pH 5.0 include, but are not limited to, those containing N-hydroxysuccinimidyl esters, imidate esters, thiolactones, carboxyanhydrides, sulfonyl halides, isourea esters, benzoquinones, vinyl sulfones, hydrazides and imidazolyl carbonyls. Typically such spacer molecules are bifunctional, wherein one end of the spacer contains an amine-reactive chemical moiety, while the other end contains the same or a different reactive species for attachment to the surface.

Whereas the spacer molecule is covalently bound to hirudin or its analogs in accordance with the present invention, the attachment of the spacer to the surface may occur by any binding means or combination of binding means, that will retain a sufficient concentration of hirudin or its analogs at the surface to provide a nonthrombogenic and anticoagulant surface under the conditions of use.

Attachment of the hirudin analog and its spacer to the surface may be by covalent means, reacting the group on the free end of the spacer with a reactive group on the surface. Alternately the hirudin-spacer conjugate may be coupled to a reactive group on the free end of a different spacer or on a macromolecule which are themselves covalently bound to the surface. The preferred chemical reactions to attach hirudin analogs to a surface or to a surface-bound spacer are those that occur rapidly and quantitatively under moderate conditions and avoid reaction with reactive amino acid side chains of hirudin and its analogs or denaturation of the molecule. Examples of such reactive pairs include, but are not limited to, thiol-maleimide, thiol-iodoacetate, and hydrazide-aldehyde (from oxidized sugar cis-diols). Alternately, the hirudin analog and its spacer may be attached to the surface by non-covalent binding means, which may include, for example, those that operate predominantly by hydrophobic binding mechanisms, or by fluorophilic associations, or by high affinity ligand receptor binding. The spacer attached to the hirudin analog may have at its free end, for example, a hydrophobic or a fluorophilic moiety that will bind directly to a similarly hydrophobic or fluorophilic surface. Or, the said spacer may have at its free end a chemical moiety that reacts to produce a covalent bond with the free end of a second spacer that is attached to the surface by non-covalent means. In another embodiment, the hirudin-attached spacer may terminate in a high affinity ligand, such as a biotin molecule, which would then bind to its high affinity receptor molecule, such as avidin, that is itself covalently bound to the surface. Or, where the high affinity receptor molecule has multiple binding sites for its ligand, the receptor molecule may be attached to the surface by binding to one of its specific ligands that is itself attached to the surface by any of the covalent or non-covalent binding means or combination of binding means just described.

The hirudin of this invention may be attached to materials which are useful in the production and use of medical products, systems and devices. Such materials include naturally occurring, genetically derived and synthetic materials. Naturally occurring materials include tissues, membranes, organs and naturally occurring polymers. One example of a genetically derived material is poly-beta-hydroxybutyrate.

Such naturally occurring, genetically derived and synthetic polymers homo- and co-polymers derived from one or more of the following: 1-olefins, such as ethylene, propylene, tetrafluoroethylene, hexafluoropropylene, vinylidene difluoride, etc.; vinyl monomers, such as vinyl chloride, styrene, maleic anhydride, methylmethacrylate, acrylonitrile, etc.; ethers, such as ethylene, tetramethylene, etc.; esters, such as ethylene-terephthalate, bisphenol A-terephthalate, etc.; carbonates, such as bisphenol A, 4,4-dihydroxybiphenylene, etc.; amides (including ureas and urethanes), such as nylons, segmented polyurethanes, proteins, etc.; saccharides, such as glucose, glucosamine, guluronic acid, sulfated glycoseaminoglycans, agarose, alginic acid, etc.; siloxanes, such as dimethyl siloxane, 3-aminopropyl siloxane, etc. Polymers which are useful in this invention may include biodegradable, partially biodegradable and non-biodegradable polymers. Other useful materials include metals, such as aluminum and stainless steel; glass, ceramics, and carbon in its various forms.

The choice of the material to which hirudin or its analogs may be attached generally depends on the function of the medical device or product incorporating that material. Given a specific material or combination of materials in a single device, or system of multiple devices, a surface attachment strategy is formulated for hirudin, following principles and logic well known to those skilled in the art. The above considerations ultimately determine the chemical group selected for the free end of the spacer attached to hirudin, and the subsequent members of the chain that retains hirudin at the material surface.

It is understood that the mechanisms described for attachment of hirudin and its analogs to surfaces in accordance with the present invention are equally applicable to their, attachment to mass-increasing molecules for the purpose of prolonging their in vivo half-life. Examples of such mass-increasing molecules include, but are not limited to, polymers such as polyethylene glycol or oxide, polyvinylpyrrolidone or the polyglucoses; and macromolecules such as serum albumin, avidin, heparin, or hydroxyethyl starch. Large, globular mass-increasing molecules may be attached to hirudin by means of a long spacer that provides hirudin with sufficient spatial freedom to achieve its inhibitory position on thrombin; or, in other words, steric interference between the mass-increasing molecule and thrombin must not block the presentation of hirudin to its binding sites on thrombin. Polyethylene glycol or oxide chains, which are generally attached directly to the macromolecule of interest, demonstrate a mass-increasing effect beyond their actual mass because of the larger excluded volume subtended by their highly mobile chains. See: Knauf, M. J. et al., J. Biol. Chem. 263 pp. 15064 to 15070 (1988). Site-directed PEGylation of hirudin at the finger region Tyr positions the mobile polyethylene glycol/oxide chains on the side of the hirudin molecule opposite from its thrombin-binding site.

EXAMPLE 1

Production of rHV2-Phe$^{3}$ GLn$^{33}$ Tyr$^{35}$ LYS$^{47}$ Asp$^{63}$ (SEQ ID NOS: 1&2) HV2 has Tyr at positions 3 and 63. In accordance with the present invention, the reactive functional Tyr$^{3}$ is replaced with nonreactive functional Phe, and the reactive functional Tyr$^{63}$ is replaced with nonreactive functional Asp. These replacements do not reduce the thrombin binding activity of the molecule. Reactive nonfunctional Tyr is then substituted for the native nonreactive nonfunctional Lys at position 35 in the finger region. This change also does not eliminate the thrombin binding activity of the molecule but it does provide a site where Tyr is available for reaction. Asn at position 47 may be changed to Lys as described in European Patent Application No. 87402696.6 to improve the activity of the antithrombogenic analog.

The hirudin analog HV2 $Phe^3$ $GLn^{33}$ $Tyr^{35}$ $LYS^{47}$ $Asp^{63}$ (SEQ ID NOS: 1&2) was prepared by the following methods:

A. Starting material

Starting material was phage M13TG4892. This phage (a derivative of M13TG131) contains an expression block consisting of:

a. a slightly modified version of the MFαl promoter (the 5' EcoRI site was converted to a SphI site, and the internal BglII site was destroyed by a treatment with the Klenow fragment of *E. coli* DNA polymerase I), b. a variant of the yeast BGL2 signal peptide (BGL2-$Val^7$), and c. the rHV2-$Lys^{47}$ coding sequence.

B. rHV2-$Lys^{47}$ $Asp^{63}$

By site directed mutagenesis (oligonucleotide OTG2942; Amersham site directed mutagenesis kit #RNP 1523) on single stranded DNA (ssDNA) of M13TG4892 the codon TAT ($Tyr^{63}$) was exchanged for GAC (Asp) resulting in M13TG5884. The mutation was verified by sequencing the entire hirudin coding sequence (sequencing primer: OTG2387). rHV2-$Lys^{47}$ $Asp^{63}$ is encoded in M13TG5884.

C. rHV2-$Phe^3$ $Gln^{33}$ $Tyr^{35}$ $Lys^{47}$ $Asp^{63}$

By site directed mutagenesis (oligonucleotides OTG2993: $Tyr^3$ to Phe and OTG2994: $Asn^{33}$ to Gln, $Lys^{35}$ to Tyr) on ssDNA of M13TG5884 the codons TAT ($Tyr^3$) were exchanged for TTC (Phe), AAT (Asn $^{33}$) for CAA (Gln), and AAG (Lys $^{35}$) for TAC (Tyr) at the same time resulting in M13TC6844. The mutations were verified by sequencing the entire hirudin coding sequence (FIG. 1). rHV2-$Phe^3$ $GLn^{33}$ $Tyr^{35}$ $LYS^{47}$ $Asp^{63}$ is encoded in M13TG6844.

D. Assembly of the expression vector pTG6864

The yeast basic expression vector pTG3828 (pBR322, 2 micron, URA3-d, PGK1 transcriptional terminator) was used to assemble the expression plasmid. Vector pTG3828 and M13TG6844 (dsDNA) were digested with SphI and SalI and ligated. The ligation mixture was used to transform *E. coli* strain BJ5183 to ampicillin resistance ($Ap^R$). Plasmid DNA was isolated from six $Ap^R$clones, and the PstI restriction profile of each preparation analyzed. Corresponding to the expected restriction profile clone N°1 was used for a CsCl purification of pTG6864 (alkaline lysis protocol). Structure of the purified plasmid was verified again by digestion with PstI and SphI+Sal1.

pTG6864: the yeast rHV2-$Phe^3$ $GLn^{33}$ $Tyr^{35}$ $LYS^{47}$ $Asp^{63}$ production plasmid (FIG. 2) is an *E. coli*-yeast shuttle vector with the following elements:

i. a bacterial segment, which is derived from *E. coli* plasmid pBR322, harboring a bacterial origin of replication (ori), and the bacterial selection marker for ampicillin resistance ($Ap^R$)

ii. a segment of the yeast 2 micron episome with its origin of replication iii. a promoter- and terminator-deleted version of the yeast URA3 gene (URA3-d) serving as a yeast selectable marker iv. a modified version of the yeast MFα1 promoter v. a sequence coding for a variant form of the yeast BGL2 derived signal peptide serving as a secretion signal fused in frame to the rHV2-Phe3 Gln33 $Tyr^{35}$ Lys47 Asp63 coding sequence, and segment of the yeast PGK gene serving as a transcriptional terminator.

Thus, pTG6864 confers ampicillin resistance to transformed *E. coli* cells; and it renders transformed yeast ura3 auxotrophic strains prototrophic for uracil ($Ura^+$).

The DNA sequence encoding rHV2-$Phe^3$ $Gln^{33}$ $Tyr^{35}$ $Lys^{47}$ $Asp^{63}$ (FIG. 1) has been verified after site directed mutagenesis, and is contained in M13TG6844 and pTG6864, respectively.

E. Transformation of yeast strain TGY48.1

Plasmid pTG6864 has been used to transform *Saccharomvces cerevisiae* strain TGY48.1 MATαura3his3 pral prbl prcl cpsl to uracil prototrophy (lithium acetate protocol; 5.5 μg of plasmid DNA per $1.3\times10^8$ cells). TGY48.1 is a haploid strain of mating type α (MATα) with a nonreverting allele of the URA3 gene (ura3-Δ5) as selectable marker. After four days incubation at 30° C. three $Ura^+$clones were obtained. Clone No°1 was further analyzed.

F. Hirudin production from TGY48.1/pTG6864

$Ura^+$prototrophy of clone N°1 was verified. Clone No°1 was grown at 30° C. in an Erlenmeyer flask (250 ml) under selective conditions for 48 hrs to a final cell density (measured as absorbance at 600 nm, where $A_{600}$=1 corresponds to $10^7$ cells/ml) of 10 to 12. Cells were centrifuged out, and culture supernatants were tested for thrombin inhibition in a kinetic assay using the chromogenic substrate, Tos-Gly-Pro-Arg-4-nitroanilide acetate (Chromozym TH, Boehringer Mannheim, Germany). Hirudin production was expressed as the anti-thrombin activity of yeast culture supernatant (ATU/ml) normalized to the $A_{600}$ of the culture.

EXAMPLE 2

Once an analog is prepared having a nonfunctional Tyr available, known methods may be employed to bind that Tyr to a spacer.

Hirudin containing an aryl amine on tyrosine (Hirudin-Tyr-$NH_2$) was prepared by nitration followed by reduction (J. F. Riordan and B. L. Vallee. Methods Enzymol. 25 pp. 515–521 (1972)). The nitration reaction was performed at room temperature in 0.01M sodium phosphate, pH 8.3, by mixing hirudin ($0.7\times10^{-6}$M) with a ten-fold molar excess of ethanolic tetranitromethane. The reaction was monitored by absorbance at 428 nanometers for 2 hours, then terminated by gel filtration on BIO-GEL ® (cross-linked polycrylamide) P-6DG pre-equilibrated with the sodium phosphate buffer. Hirudin-Tyr-$NO_2$ was reduced to hirudin-Tyr-$NH_2$ by adding a ten-fold molar excess of sodium dithionite in the sodium phosphate buffer and incubating until the nitrophenol absorbance at 428 nanometers disappeared. The aryl amino (tyrosine) hirudin was separated from excess sodium dithionite by desalting on BIO-GEL ® P-6DG pre-equilibrated with 0.04M sodium acetate, pH 5.0, concentrated and stored at −20° C.

EXAMPLE 3

Attachment of SPDP to Hirudin-Tyr-$NH_2$

Sulfo-LC-SPDP (Sulfosuccinimidyl 6-[3-(2-pyridyldithio) propionamido] hexanoate) was attached to hirudin containing an aryl amine on tyrosine by the following method: To hirudin-Tyr-$NH_2$ ($0.143\times10^{-6}$M) in 0.04M sodium acetate, pH 5.0, was added a ten-fold molar excess of Sulfo-LC-SPDP and the solution agitated for 2 hours at room temperature. Excess Sulfo-LC-SPDP was removed by desalting on BIO-GEL® P-6DG pre-equilibrated with 0.01M sodium phosphate, pH 7.0, and the SPDP-hirudin concentrated and stored at −20° C. The LC-SPDP-hirudin was incubated before use with a 3-fold molar excess of dithiothreitol in 0.04M sodium acetate, 0.005M EDTA, pH 4.5, until absorbance at 343 nanometers reached a plateau, then the LC-SPDP-hirudin was purified by desalting on BIO-GEL® P-6DG.

EXAMPLE 4

Binding N-Acetyl-homocysteine to Hirudin-Tyr-$NH_2$

N-Acetyl-homocysteine was attached to hirudin that contained an aryl amine on tyrosine by the following method: Into a solution of hirudin-Tyr-$NH_2$ ($0.143\times10^{-6}$M) in 0.04M sodium acetate, pH 5.0, was mixed a ten-fold molar excess of N-acetyl-homocysteine thiolactone (AHTL) in methanol and reaction continued for two hours with constant agitation at room temperature. Excess AHTL was removed by desalting on BIO-GEL® P-6DG pre-equilibrated with 0.01M sodium phosphate, pH 7.0, and the N-acetyl-homocysteine-hirudin concentrated and stored at −20° C. All reactions were performed under a stream of nitrogen gas.

EXAMPLE 5

Surface immobilization of hirudin-spacer conjugates by thiol ethers

Sulfo-LC-SPDP-or N-acetyl-homocysteine-hirudin was attached to surfaces by formation of a thiol ether bond. In brief, an agarose gel bearing either a long-chain iodoacetyl group (0.5 ml SULFOLINK GEL® (cross-linked agarose, Pierce) or a maleimide (SulfOSMCC: Sulfosuccinimidyl 4-(maleimidomethyl) cyclohexane-1-carboxylate) was reacted with either of the above hirudin derivatives ($1.43\times10^{-6}$M in 0.05M Tris-HCl, 0.005M EDTA-Na, pH 8.5) for 1 hour at room temperature. The gel was washed with 0.05M Tris, 0.005M EDTA-Na, pH 8.5; incubated with 0.05M cysteine, 0.05M Tris, 0.005M EDTA-Na, pH 8.5 for 1 hour; washed with 1M NaCl; then equilibrated with physiological saline, pH 7.2.

EXAMPLE 6

Binding of NHS-LC-Biotin to Hirudin-Tyr-$NH_2$

NHS-LC-biotin (Sulfosuccinimidyl-6-(biotinamido) hexanoate) was attached to hirudin containing an aryl amine on tyrosine by the following method: To hirudin-Tyr-$NH_2$ ($0.143\times10^{-6}$M) in 0.04M sodium acetate, pH 5.0, was added a ten-fold molar excess of NHS-LC-biotin and the solution agitated for 2 hours at room temperature. Excess LC-biotin was removed by desalting on BIO-GEL® P-6DG.

EXAMPLE 7

Attachment of Hirudin-Spacer Coniuqates by Avidin-Biotin Complexes

Hirudin-Tyr-LC-biotin conjugates were bound to soluble avidin, avidin-coated polystyrene beads (FLUORICON particles, Baxter Healthcare) or avidin-coated silicone rubber tubing at a 1:1 molar ratio by incubating in 0.02M sodium phosphate pH 7.4 for 1 hour at room temperature.

EXAMPLE 8

Anti-thrombin activity of attached hirudin analogs

The thrombin inhibition activity of rHV2-$Phe^3$ $Gln^{33}$ $Tyr^{35}$ $Lys^{47}$ $Asp^{63}$: (H-Tyr), and its derivatives, including spacer molecules ranging from 200 to 67,000 molecular weight, were determined by incubating them with human thrombin, then measuring the residual thrombin activity as the initial velocity of amidolysis of H-D-Phenylalanyl-L-pipecolyl-L-arginine-p-nitroanalide dihydrochloride (Kabi, S-2238), where zero thrombin activity was 100% inhibition. Aliquots containing 0.13–1.3 picomoles of hirudin as (a) the analog, H-Tyr, (b) the analog with an aryl amine on $Tyr^{35}$: (H-Tyr-$NH_2$), (c) the analog with LC-biotin attached to the tyrosyl amine: (H-Tyr-B), (d) the biotinylated analog attached to soluble avidin: (H-Tyr-B-Av), (e) the biotinylated analog attached to avidin-coated beads: (H-Tyr-B-Av-Beads), (f) the analog with N-acetyl-homocysteine attached to the tyrosyl amine and to SULFOLINK GEL® (H-Tyr-AH-SLG), and (g) the analog with LC-SPDP attached to the tyrosyl amine and to SULFOLINK GEL® (H-Tyr-SPDP-SLG); were reacted with 1.3 picomoles of human alpha-thrombin in 0.05M Tris-HCl, pH 7.4, 0.1% bovine serum albumin, for 1 hour at 22° C.; then centrifuged. Aliquots of the supernatants were diluted with the Tris-BSA buffer and the reaction initiated by addition of S-2238. Reaction velocities were monitored at 410 nanometers and used to determine thrombin activity. Moles of hirudin analog and its derivatives in each assay were determined by radioiodinated hirudin analog tracer. The analog H-Tyr retained virtually all of its specific thrombin inhibition activity during insertion of an amine into the tyrosine ring, attachment of LC-biotin spacer, and when bound through the spacer to soluble avidin or to avidin-coated beads. However, when the analog was attached to a surface via the shorter spacer molecules, diminished specific thrombin inhibitory activity was observed (Table I).

TABLE I

| Hirudin Analog | Thrombin Inhibition (Specific Activity: *% of H—Tyr) |
|---|---|
| H—Tyr | 100 |
| H—Tyr—$NH_2$ | 99 |
| H—Tyr—B | 99 |
| H—Tyr—B—AV | 98 |
| H—Tyr—B—Av—Beads | 97 |
| H—Tyr—AH—SLG | 6 |
| H—Tyr—SPDP—SLG | 61 |

EXAMPLE 9

Preparation and anti-thrombin activity of hirudin-Tyr-PEG adduct.

To provide a soluble hirudin of increased mass similar to the biotinylated hirudin attached through a spacer to soluble avidin as described in Examples 7 and 8, methoxypolyethylene glycol (5 kD) was directly bound to hirudin through an aryl amine on tyrosine by reacting hirudin-Tyr-$NH_2$, $0.143\times10^{-6}$M in 0.04M sodium acetate, pH 5.0, with a fifty-fold molar excess of methoxypolyethylene glycol-succinimidyl succinate (MPEGSS) for 30 min at room temperature. The reaction was stopped by addition of excess glycine at pH 7 to inactivate residual MPEGSS. SDS-PAGE analysis of the reaction products demonstrated complete transformation of hirudin-Tyr-$NH_2$ to its PEG adduct. The adduct retained 90% of the thrombin inhibitory activity of the hirudin-Tyr-$NH_2$ starting material when evaluated by the chromogenic assay described in Example 8. This illustrates that mass-increasing PEG derivatives can be directly attached to rHV2-$Phe^3$ $Gln^{33}$ $Tyr^{35}$ $Lys^{47}$ $Asp^{63}$ (SEQ ID NOS: 1 & 2) through an aryl amine in the phenolic ring of $Tyr^{35}$ without significant loss of biological activity.

What is claimed is:

1. An antithrombogenic molecule having the amino acid sequence of (SEQ ID NO: 2).

* * * * *